United States Patent [19]

Flanigen et al.

[11] Patent Number: 5,057,295

[45] Date of Patent: Oct. 15, 1991

[54] BORON-ALUMINUM-PHOSPHORUS-SILICON-OXIDE MOLECULAR SIEVE COMPOSITIONS

[75] Inventors: Edith M. Flanigen, White Plains, N.Y.; Richard T. Gajek, New Fairfield, Conn.; Brent M. T. Lok, New City, N.Y.; Robert L. Patton, Katonah, N.Y.; Stephen T. Wilson, Shrub Oak, N.Y.

[73] Assignee: UOP, Des Plaines, Ill.

[21] Appl. No.: 845,255

[22] Filed: Mar. 28, 1986

Related U.S. Application Data

[63] Continuation-in-part of Ser. No. 600,177, Apr. 13, 1984, abandoned.

[51] Int. Cl.$^5$ .............................................. C01B 35/00
[52] U.S. Cl. ..................................... 423/277; 423/328
[58] Field of Search ............... 423/305, 306, 277, 328, 423/329; 502/214, 208

[56] References Cited

U.S. PATENT DOCUMENTS

| | | | |
|---|---|---|---|
| 3,328,119 | 6/1967 | Robson | 423/277 |
| 3,586,479 | 6/1971 | Heinze et al. | 423/328 M |
| 4,269,813 | 5/1981 | Klotz | 423/277 |
| 4,440,871 | 4/1984 | Lok et al. | 502/214 |
| 4,647,442 | 3/1987 | Derouane et al. | 423/305 |

FOREIGN PATENT DOCUMENTS

| | | | |
|---|---|---|---|
| 0087189 | 5/1983 | Japan | 502/214 |
| 0984502 | 2/1965 | United Kingdom | 423/328 M |

Primary Examiner—John Doll
Assistant Examiner—R. Bruce Breneman
Attorney, Agent, or Firm—Thomas K. McBride; Eugene I. Snyder; Frank S. Molinaro

[57] ABSTRACT

Molecular sieve compositions having three-dimensional microporous framework structures of $BO_2$, $AlO_2$, $PO_2$ and $SiO_2$ tetrahedral oxide units are disclosed. These molecular sieves have an empirical chemical composition on an anhydrous basis expressed by the formula:

$$mR:(B_wAl_xP_ySi_z)O_2$$

wherein "R" represents at least one organic templating agent present in the intracrystalline port system; "m" represents the molar amount of "R" present per mole of $(B_wAl_xP_ySi_z)O_2$; and "w", "x", "y" and "z" represent the mole fraction of boron, aluminum, phosphorus and silicon, respectively, present as tetrahedral oxides. Their use as adsorbents, catalysts, etc. is also disclosed.

29 Claims, 3 Drawing Sheets

BORON-ALUMINUM-PHOSPHORUS-SILICON-OXIDE MOLECULAR SIEVE COMPOSITIONS

This application is a continuation-in-part of our co-pending application Ser. No. 600,177 filed Apr. 13, 1984 and now abandoned.

Field of the Invention

The instant invention relates to a novel class of crystalline microporous molecular sieves and to the method of their preparation. The invention relates to novel boron-aluminum-phosphorus-silicon-oxide molecular sieves containing framework tetrahedral oxide units of boron, aluminum, phosphorus and silicon. These compositions may be prepared hydrothermally from gels containing reactive compounds of boron, aluminum, phosphorus and silicon capable of forming framework tetrahedral oxides, and preferably at least one organic templating agent which functions in part to determine the course of the crystallization mechanism and the structure of the crystalline product.

Background of the Invention

Molecular sieves of the crystalline alumino-silicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the alumino-phosphate molecular sieves are moderately hydrophilic, apparently due to the difference in electronegativity between aluminum and phosphorus. Their intracrystalline pore volumes and pore diameters are comparable to those known for zeolites and silica molecular sieves.

In U.S. Pat. No. 4,440,871, there is described a novel class of silicon-substituted alumino-phosphates which are both microporous and crystalline. The materials have a three dimensional crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

mR : $(Si_xAl_yP_z)O_2$ wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In U.S. Pat. No. 4,500,651, there is described a novel class of titanium-containing molecular sieves whose chemical composition in the as-synthesized and anhydrous form is represented by the unit empirical formula:

mR: $(Ti_xAl_yP_z)O_2$ wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In U.S. Pat. No. 4,567,029, there is described a novel class of crystalline metal alumino-phosphates having three-dimensional microporous framework structures of $MO_2$, $AlO_2$ and $PO_2$ tetrahedral units and having an empirical chemical composition on an anhydrous basis expressed by the formula:

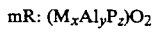

mR: $(M_xAl_yP_z)O_2$ wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; "x", "y", and "z" represent the mole fractions of the metal "M", aluminum and phosphorus, respectively, present as tetrahedral oxides.

In U.S. Pat. No. 4,544,143, there is described a novel class of crystalline ferroaluminophosphates having a three-dimensional microporous framework structure of $FeO_2$, $AlO_2$ and $PO_2$ tetrahedral units and having an empirical chemical composition on an anhydrous basis expressed by the formula

mR:$(Fe_xAl_yP_z)O_2$ wherein "R" represents at least one organic templating agent present in the intracrystalline pore system; "m" represents the moles of "R" present per mole of $(Fe_xAl_yP_z)O_2$ and has a value of from zero to 0.3; and "x", "y" and "z" represent the mole fractions of the iron, aluminum and phosphorus, respectively, present as tetrahedral oxides.

The instant invention relates to new molecular sieve compositions comprising framework tetrahedral units of $BO_2^-$, $AlO_2^-$, $PO_2^+$ and $SiO_2$.

SUMMARY OF THE INVENTION

Figure 1:
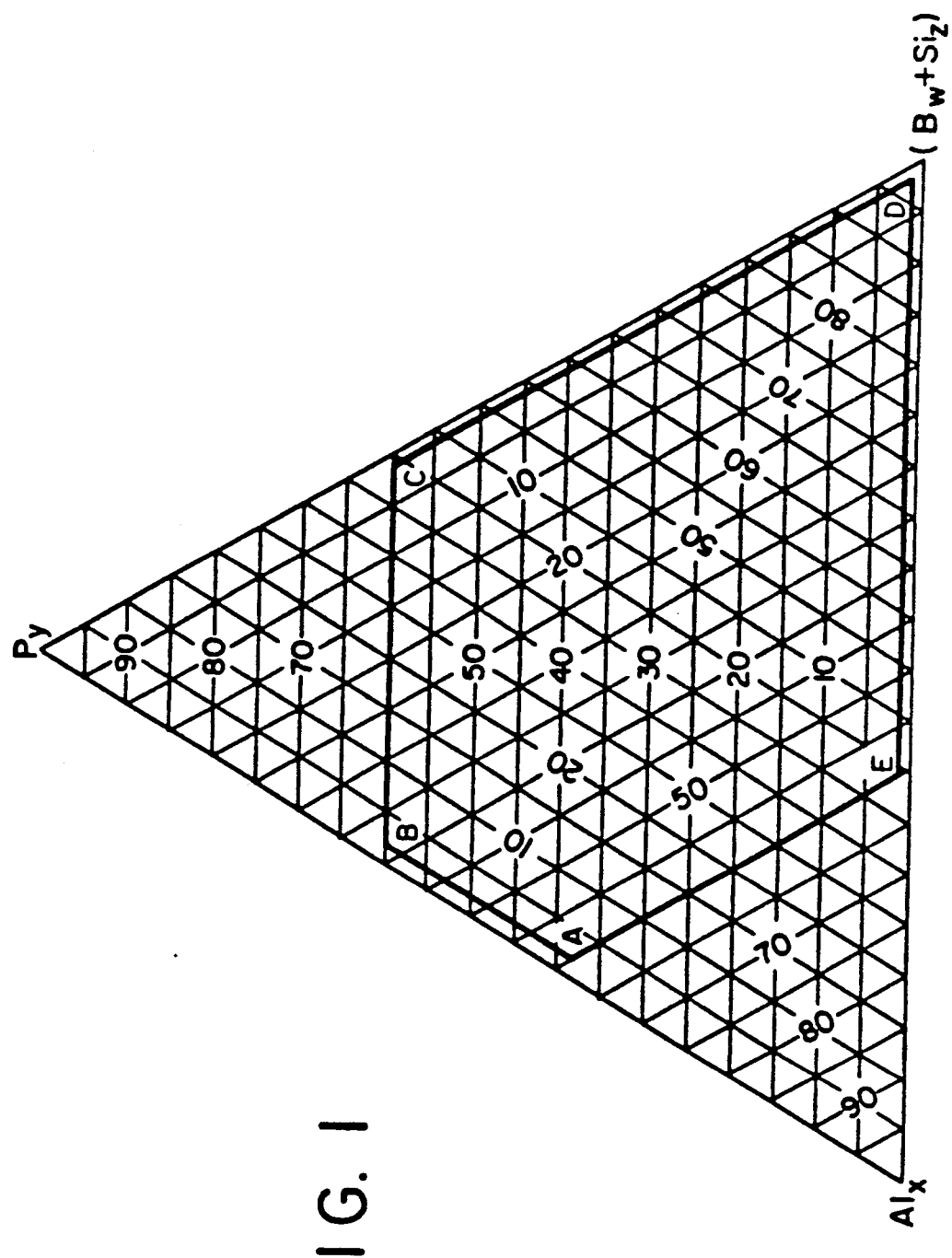
FIG. 1 is a ternary diagram wherein parameters relating to the instant compositions are set forth as mole fractions.

The instant invention relates to a new class of boron-aluminum-phosphorus-silicon-oxide molecular sieves having a crystal framework structure of $BO_2^-$, $AlO_2^-$, $PO_2^+$ and $SiO_2$ tetrahedral oxide units. These new molecular sieves exhibit ion-exchange, adsorption and catalytic properties and, accordingly, find wide use as adsorbents and catalysts. The members of this novel class of compositions have crystal framework structures of $BO_2^-$, $AlO_2^-$, $PO_2^+$ and $SiO_2$ tetrahedral units and have an empirical chemical composition on an anhydrous basis expressed by the formula:

mR $(B_wAl_xP_ySi_z)O_2$ wherein "R" represents at least one organic templating agent present in the intracrystalline pore system; "m" represents the molar amount of "R" present per mole of $(B_wAl_xP_ySi_z)O_2$ and has a value of zero to about 0.3; and "w", "x", "y" and "z" represent the mole fractions of boron, aluminum, phosphorus and silicon, respectively, present as tetrahedral oxides. These molecular sieve compositions comprise crystalline molecular sieves having a three-dimensional microporous framework structure of $BO_2^-$, $AlO_2^-$, $PO_2^+$ and $SiO_2$ tetrahedral units.

The instant molecular sieve compositions are characterized in several ways as distinct from heretofore known molecular sieves, including the aforementioned ternary compositions. The instant molecular sieves are characterized by the enhanced thermal stability of certain species and by the existence of species heretofore unknown for binary and ternary molecular sieves.

The molecular sieves of the instant invention will be generally referred to by the acronym "BAPSO" to designate the framework of $BO_2^-$, $AlO_2^-$, $PO_2^+$ and $SiO_2$ tetrahedral units. Actual class members will be identified by denominating the various structural species which make up the BAPSO class by assigning a number and, accordingly, are identified as "BAPSO-i" wherein "i" is an integer. This designation is an arbitrary one and is not intended to denote structural relationship to another material(s) which may also be characterized by a numbering system.

DETAILED DESCRIPTION OF THE INVENTION

The instant invention relates to a new class of boron-aluminum-phosphorus-silicon-oxide molecular sieves comprising a crystal framework structure of $BO_2^-$, $AlO_2^-$, $PO_2^+$ and $SiO_2$ tetrahedral oxide units. These new molecular sieves exhibit ion-exchange, adsorption and catalytic properties and, accordingly, find wide use as adsorbents and catalysts.

The BAPSO molecular sieves of the instant invention comprise a framework structure of $BO_2^-$, $AlO_2^-$, $PO_2^+$ and $SiO_2$ tetrahedral units having an empirical chemical composition on an anhydrous basis expressed by the formula:

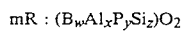

mR : $(B_wAl_xP_ySi_z)O_2$ wherein "R" represents at least one organic templating agent present in the intracrystalline pore system; "m" represents the molar amount of "R" present per mole of $(B_wAl_xP_ySi_z)O_2$ and has a value of zero to about 0.3, but is preferably not greater than about 0.15; and "w", "x", "y" and "z" represent the mole fractions of boron, aluminum, phosphorus and silicon, respectively, present as tetrahedral oxides. The mole fractions "w", "x", "y" and "z" are generally defined as being within the pentagonal compositional area defined by points A, B, C, D and E of the ternary diagram of FIG. 1. Points A, B, C, D and E of FIG. 1 have the following values for "w", "x", "y", and "z":

| Point | Mole Fraction | | |
|---|---|---|---|
| | x | y | z + w |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

Figure 2:
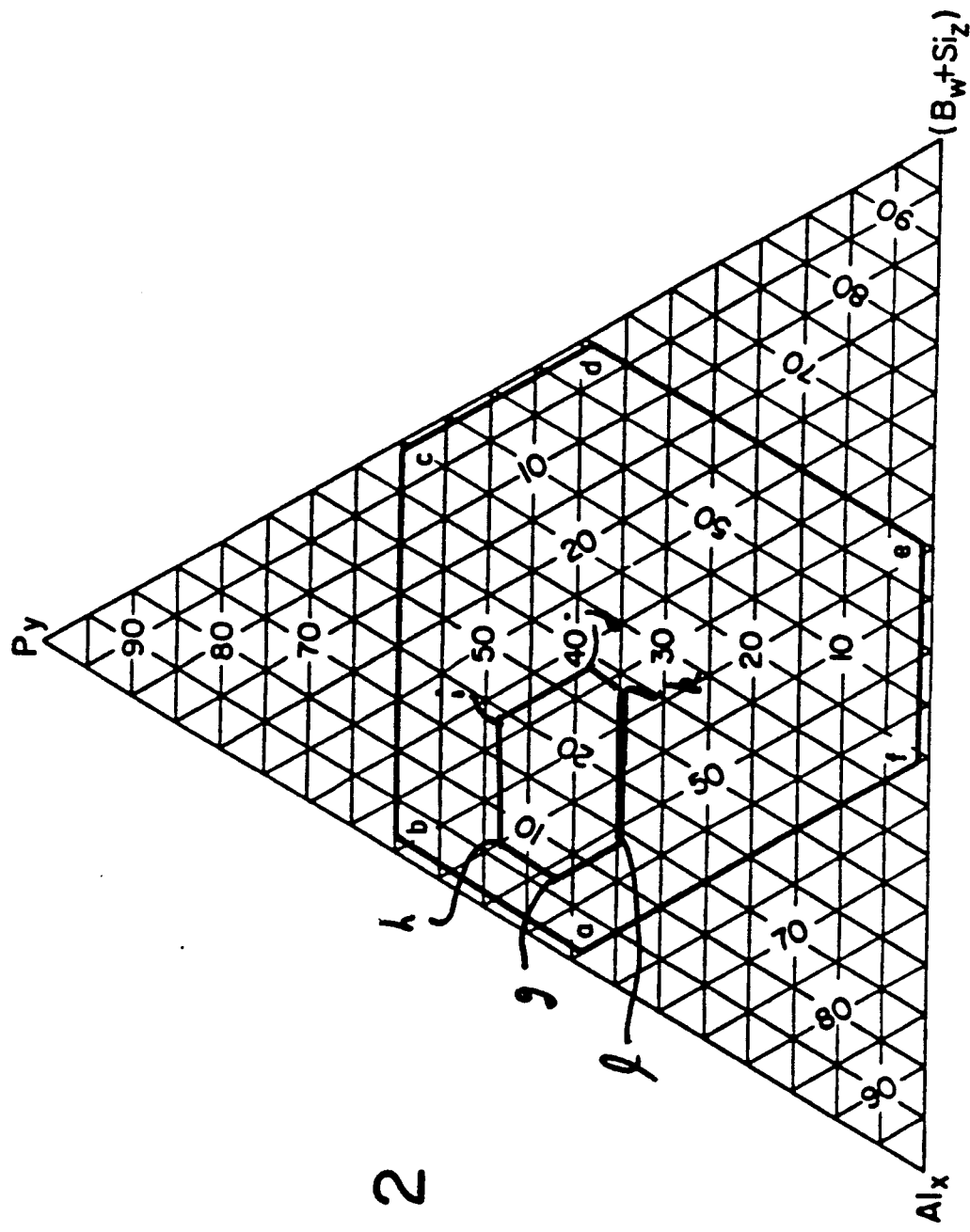
FIG. 2 is a ternary diagram wherein parameters relating to preferred compositions are set forth as mole fractions.

In a preferred subclass of the SAPSO molecular sieves the values of "w", "x", "y" and "z" in the above formula are within the hexagonal compositional area defined by the points a, b, c, d, e and f of the ternary diagram which is FIG. 2 of the drawings, said points a, b, c, d, e and f representing the following values for "w", "x", "y" and "z":

| Point | Mole Fraction | | |
|---|---|---|---|
| | x | y | z + w |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the BAPSO molecular sieves the values of "w", "x", "y" and "z" in the above formula are within the hexagonal compositional area defined by the points g, h, i, j, k and l of the ternary diagram which is FIG. 2 of the drawings, said points g, h, i, j, k and l representing the following values for "w", "x", "y" and "z":

| Point | Mole Fraction | | |
|---|---|---|---|
| | x | y | z + w |
| g | 0.51 | 0.42 | 0.07 |
| h | 0.45 | 0.48 | 0.07 |
| i | 0.33 | 0.48 | 0.19 |
| j | 0.33 | 0.38 | 0.29 |
| k | 0.36 | 0.35 | 0.29 |

| Point | Mole Fraction | | |
|---|---|---|---|
| | x | y | z + w |
| 1 | 0.51 | 0.35 | 0.14 |

The BAPSOs of this invention are useful as adsorbents, catalysts, ion-exchangers, and the like in much the same fashion as aluminosilicates have been employed heretofore, although their chemical and physical properties are not necessarily similar to those observed for aluminosilicates.

BAPSO compositions are generally synthesized by hydrothermal crystallization from a reaction mixture containing reactive sources of boron, aluminum, phosphorus and silicon, preferably an organic templating, i.e., structure-directing agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure, at a temperature between 50° C. and 250° C., and preferably between 100° C. and 200° C., until crystals of the BAPSO product are obtained, usually for a period of from several hours to several weeks. Crystallization times of from about 2 hours to about 30 days are generally employed with from about 4 hours to about 20 days being typically employed. The product is recovered by any convenient method such as centrifugation or filtration.

In synthesizing the BAPSO compositions of the instant invention, it is preferred to employ a reaction mixture composition expressed in terms of the molar ratios as follows:

$$aR:(B_sAl_tP_uSi_v)O_2: bH_2O$$

wherein "R" is an organic templating agent; "a" is the amount of organic templating agent "R" and has a value within the range of greater than zero (0) to about 6 and most preferably not more than about 0.5; "b" has a value of between zero (0) and about 500, preferably between about 2 and about 300, most preferably not more than about 20; and —s—,—t—, —v—and—v—represent the mole fractions of boron, aluminum, phosphorus and silicon, respectively, and each has a value of at least 0.01.

Figure 3:
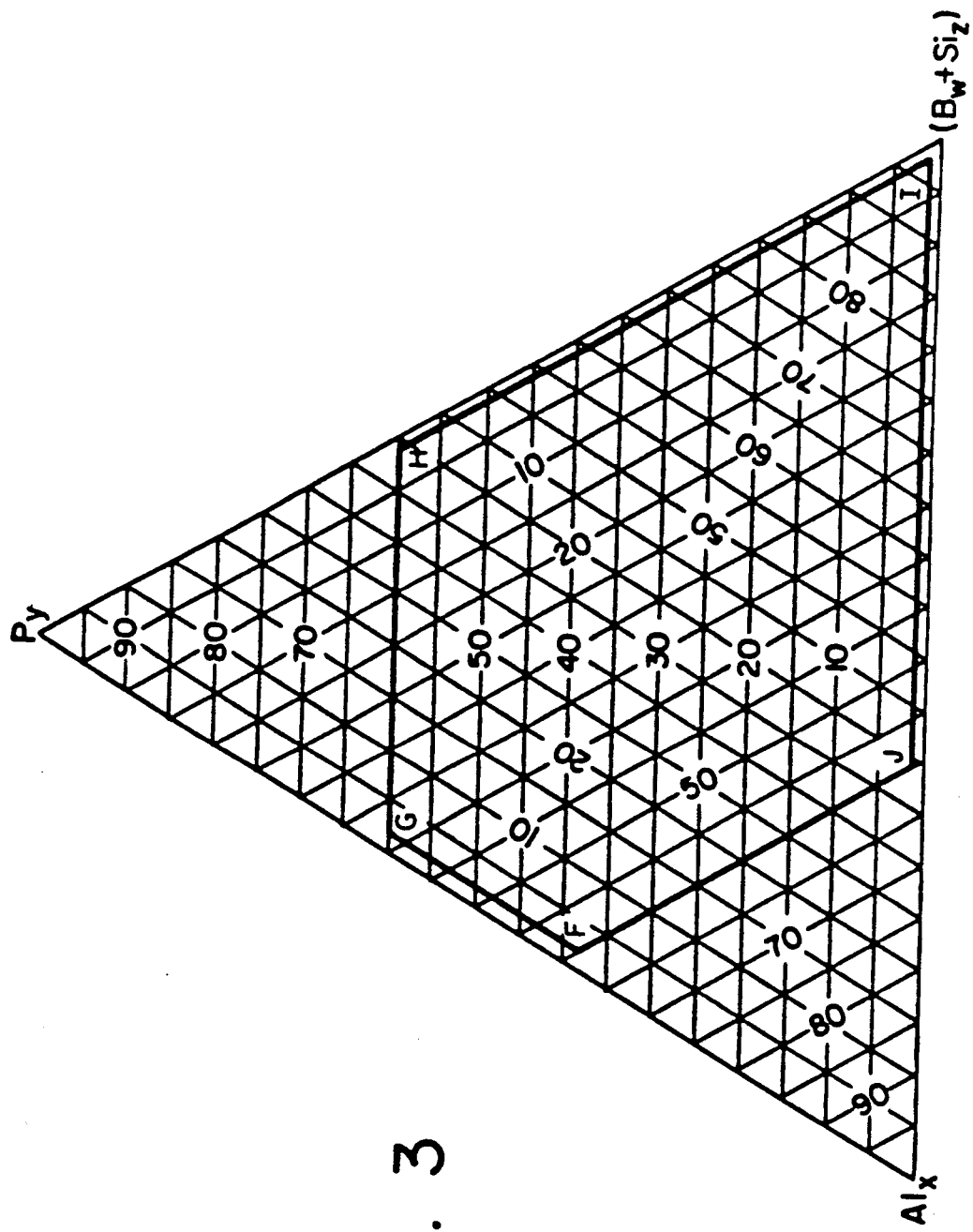
FIG. 3 is a ternary diagram wherein parameters relating to the reaction mixtures employed in the preparation of the compositions of this invention are set forth as mole fractions.

In a preferred embodiment the reaction mixture is selected such that the mole fractions —s—,—t—, —u— —and —v— are generally defined as being within the pentagonal compositional area defined by points F, G, H, I and J of the ternary diagram of FIG. 3. Points F, G, H, I and J of FIG. 3 have the following values for —s—, —t—, —v—and—v—:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Particularly preferred reaction mixture compositions are those containing from about 1.0 to about 1.5 total moles of boron and silicon, and from about 0.75 to about 1.25 moles of aluminum, per mole of phosphorus.

In the foregoing expression of the reaction composition, the reactants are normalized with respect to the total of —s—, —t—, —u—and—v—such that (w+x+y+z)=1.00 mole, whereas in the examples the reaction mixtures are expressed in terms of molar oxide ratios normalized to the moles of $P_2O_5$ or $Al_2O_3$. These latter forms are readily converted to the former form by routine calculations by dividing the number of moles of each component (including the template and water) by the total number of moles of boron, aluminum, phosphorus and silicon which results in normalized mole fractions based on total moles of the aforementioned components.

In forming reaction mixtures from which the instant molecular sieves are formed the organic templating agent can be any of those heretofore proposed for use in the synthesis of conventional zeolite alumino-silicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium and quaternary ammonium compounds, the latter two being represented generally by the formula $R_4X^+$ wherein "X" is phosphorus or nitrogen and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired BAPSOs or the more strongly directing templating species may control the course of the reaction with the other templating species serving primarily to establish the pH conditions of the reaction gel. Representative templating agents include tetramethylammonium; tetraethylammonium; tetrapropylammonium; and tetrabutylammonium ions; tetrapentylammonium ions; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2,) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; iso-propylamine; t-butylamine; ethylenediamine; pyrrolidine; and 2-imidazolidone. Not every templating agent will direct the formation of every species of BAFSO, i.e., a single templating agent can, with proper manipulation of the reaction conditions, direct the formation of several BAPSO compositions, and a given BAPSO composition can be produced using several different templating agents.

The reactive phosphorus source is preferably phosphoric acid, but organic phosphates such as triethyl phosphate have been found satisfactory, and so also have crystalline or amorphous aluminophosphates such as the AlPO4 composition of U.S. Pat. No. 4,310,440.

Organo-phosphorus compounds, such as tetrabutylphosphonium bromide, do not, apparently, serve as reactive sources of phosphorus, but these compounds do function as templating agents. Conventional phosphorus salts, such as sodium metaphosphate, may be used, at least in part, as the phosphorus source, but are not preferred.

Almost any reactive silicon source may be employed such that $SiO_2$ tetrahedral units are formed in situ. The reactive silicon source may be silica in the form of a silica sol, may be a fumed silica or may be other conventional sources of silica used in zeolite synthesis such as reactive solid amorphous precipitated silicas, silica gel, alkoxides of silicon (i.e. tetraalkyl orthosilicates such as tetraethyl orthosilicate), silicic acid, alkali metal silicates and the like.

The preferred aluminum source is either an aluminum alkoxide, such as aluminum isopropoxide tri-sec-butoxide or hexadecoxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive source of boron can be introduced into the reaction system in any form which permits the formation in situ of a reactive form of boron, i.e., reactive to form the framework tetrahedral oxide unit of boron. Compounds of boron which may be employed include oxides, alkoxides, hydroxides, chlorides, bromides, iodides, sulfates, nitrates, carboxylates (e.g., acetates) and the like. Preferred boron sources are boric acid and trialkyl borates.

While not essential to the synthesis of BAPSO compositions, stirring or other moderate agitation of the reaction mixture and/or seeding the reaction mixture with seed crystals of either the BAPSO species to be produced or a topologically similar aluminophosphate or aluminosilicate composition, facilitates the crystallization procedure.

After crystallization the BAPSO product may be isolated and advantageously washed with water and dried in air. The as-synthesized BAPSO generally contains within its internal pore system at least one form of the templating agent employed in its formation. Most commonly the organic moiety derived from an organic template is present, at least in part, as a charge-balancing cation as is generally the case with as-synthesized aluminosilicate zeolites prepared from organic-containing reaction systems. It is possible, however, that some or all of the organic moiety is an occluded molecular species in a particular BAPSO species. As a general rule the templating agent, and hence the occluded organic species, is too large to move freely through the pore system of the BAPSO product and must be removed by calcining the BAPSO at temperatures of 200° C. to 700° C. to thermally degrade the organic species. In a few instances the pores of the BAPSO product are sufficiently large to permit transport of the templating agent, particularly if the latter is a small molecule, and accordingly complete or partial removal thereof can be accomplished by conventional desorption procedures such as are carried out in the case of zeolites. It will be understood that the term "as-synthesized" as used herein does not include the condition of the BAPSO phase wherein the organic moiety occupying the intracrystalline pore system as a result of the hydrothermal crystalline process has been reduced by post-synthesis treatment such that the value of "m" in the composition formula:

$$mR\ (B_wAl_xP_ySi_z)O_2$$

has a value of less than 0.02. The other symbols of the formula are as defined hereinabove. In those preparations in which an alkoxide is employed as the source of boron, aluminum, phosphorous and/or silicon, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized BAPSO material.

Since the present BAPSO compositions are formed from $BO_2$, $AlO_2$, $PO_2$ and $SiO_2$ tetrahedral units which, respectively, have a net charge of $-1$, $-1$, $+1$ and 0, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton ($H^+$), a cation of boron present in the reaction mixture, or an organic cation derived from the templating agent. Similarly, a $BO_2^-$ tetrahedron can be balanced electrically by association with $PO_2^+$ tetrahedra, a simple cation such as an alkali metal cation, a proton ($H^+$), a cation of boron present in the reaction mixture, organic cations derived from the templating agent, or other divalent or polyvalent metal cations introduced from an extraneous source. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, DC (1971)].

The BAPSO compositions of the present invention may exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of BAPSO compositions is ordinarily possible only after the organic moiety present as a result of synthesis has been removed from the pore system. Dehydration to remove water present in the as-synthesized BAPSO compositions can usually be accomplished, to some degree at least, in the usual manner without removal of the organic moiety, but the absence of the organic species greatly facilitates adsorption and desorption procedures. The BAPSO materials will have various degrees of hydrothermal and thermal stability, some being quite remarkable in this regard, and will function as molecular sieve adsorbents and hydrocarbon conversion catalysts or catalyst bases.

In preparing the BAPSO composition it is preferred to use a stainless steel reaction vessel lined with an inert plastic material, e.g., polytetrafluoroethylene, to avoid contamination of the reaction mixture. In general, the final reaction mixture from which each BAPSO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, it is preferred that the intermediate mixtures as well as the final reaction mixtures be stirred until substantially homogeneous.

X-ray patterns of reaction products are obtained by X-ray analysis, using standard X-ray powder diffraction techniques. The radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as 2θ where θ is the Bragg angle as observed on the strip chart. Intensities were determined from the heights of diffraction peaks after subtracting background, "$I_o$" being the intensity of the strongest line or peak, and "I" being the intensity of each of the other peaks. Alternatively, the X-ray patterns may be obtained by use of computer based techniques using copper K-alpha radiation, Siemens type K-805 x-ray sources and Siemens D-500 X-ray powder diffractometers available from Siemens Corporation, Cherry Hill, N.J., with appropriate computer interface.

As will be understood by those skilled in the art, the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

In certain instances hereinafter in the illustrative examples, the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their X-ray powder diffraction patterns and as such may have one of the X-ray patterns set forth in the following Tables A through X, wherein said X-ray patterns are for the as-synthesized form unless otherwise noted. In most cases, the pattern of the corresponding calcined form will also fall within the relevant Table. However, in some cases the removal of the occluded templating agent which occurs during calcination will be accompanied by sufficient relaxation of the lattice to shift some of the lines slightly outside the ranges specified in the relevant Table. In a small number of cases, calcination appears to cause more substantial distortions in the crystal lattice, and hence more significant changes in the X-ray powder diffraction pattern.

TABLE A

| 2θ | (BAPSO-5) d(Å) | Relative Intensity |
|---|---|---|
| 7.2–7.7 | 12.28–11.48 | m–vs |
| 19.4–19.9 | 4.58–4.46 | w–m |
| 20.85–21.3 | 4.26–4.17 | w–vs |
| 22.1–22.6 | 4.02–3.93 | m–vs |
| 25.6–26.1 | 3.480–3.414 | vw–m |

TABLE B

| 2θ | (BAPSO-11) d(Å) | Relative Intensity |
|---|---|---|
| 7.8–8.2 | 11.19–10.85 | m–s |
| 9.0–9.8 | 9.83–9.03 | vw–vs |
| 12.8–13.6 | 6.92–6.51 | vw–m |
| 19.9–20.5 | 4.46–4.33 | m–s |
| 20.8–21.8 | 4.27–4.08 | m–vs |
| 22.0–22.6 | 4.04–3.93 | m–vs |
| 22.6–23.1 | 3.93–3.85 | vw–vs |
| 23.1–23.5 | 3.85–3.79 | w–vs |

TABLE C

| 2θ | (BAPSO-14) d (Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D

| 2θ | (BAPSO-16) d(Å) | Relative Intensity |
|---|---|---|
| 11.3–11.6 | 7.83–7.63 | w–vs |
| 18.55–18.9 | 4.78–4.70 | vw–m |
| 21.85–22.2 | 4.07–4.00 | m–vs |
| 22.8–23.3 | 3.900–3.818 | w–m |
| 26.4–27.3 | 3.370–3.267 | w–m |
| 29.6–29.9 | 3.018–2.988 | w–m |

TABLE E

| 2θ | (BAPSO-17) d(Å) | Relative Intensity |
|---|---|---|
| 7.70–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F

| 2θ | (BAPSO-18) d (Å) | Relative Intensity |
|---|---|---|
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE G

| 2θ | (BAPSO-20) d(Å) | Relative Intensity |
|---|---|---|
| 13.8–14.2 | 6.42–6.23 | m–vs |
| 19.6–20.15 | 4.53–4.41 | m |
| 24.1–24.7 | 3.695–3.603 | m–vs |
| 27.9–28.6 | 3.198–3.121 | w |
| 31.3–32.05 | 2.861–2.791 | w |
| 34.35–35.0 | 2.610–2.601 | w–m |

TABLE H

| 2θ | (BAPSO-31) d(Å) | Relative Intensity |
|---|---|---|
| 8.4–9.5 | 10.53–9.31 | w–s |
| 20.2–20.4 | 4.40–4.35 | m |
| 22.0–22.1 | 4.040–4.022 | m |
| 22.5–22.7 | 3.952–3.92 | vs |
| 31.6–31.8 | 2.831–2.814 | w–m |

TABLE J*

| 2θ | (BAPSO-33) d(Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

| 2θ | (BAPSO-33) d(Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| 2θ | (BAPSO-34) d(Å) | Relative Intensity |
|---|---|---|
| 9.3–9.8 | 9.51–9.03 | m–vs |
| 12.6–13.2 | 7.03–6.71 | w–m |
| 15.8–16.3 | 5.61–5.44 | vw–m |
| 20.25–21.2 | 4.39–4.19 | w–vs |
| 24.8–25.4 | 3.59–3.507 | vw–m |
| 30.0–30.9 | 2.979–2.894 | vw–m |

TABLE M

| 2θ | (BAPSO-35) d(Å) | Relative Intensity |
|---|---|---|
| 10.6–11.1 | 8.35–7.97 | vw–vs |
| 13.1–13.7 | 6.76–6.46 | vw–vs |
| 17.0–17.6 | 5.22–5.04 | w–s |
| 20.6–21.25 | 4.31–4.18 | vw–m |
| 21.6–22.3 | 4.11–3.99 | m–vs |
| 28.1–28.8 | 3.175–3.100 | vw–m |

TABLE N

| 2θ | (BAPSO-36) d(Å) | Relative Intensity |
|---|---|---|
| 7.45–8.0 | 11.14–11.05 | vs |
| 8.1–8.3 | 10.91–10.65 | w–m |

TABLE N-continued

| 2θ | (BAPSO-36) d(Å) | Relative Intensity |
|---|---|---|
| 16.3–16.6 | 5.44–5.34 | w–m |
| 18.9–19.4 | 4.70–4.57 | w–m |
| 20.7–21.0 | 4.29–4.23 | w–m |

TABLE O

| 2θ | (BAPSO-37) d(Å) | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| 2θ | (BAPSO-39) d(Å) | Relative Intensity |
|---|---|---|
| 9.2–9.6 | 9.61–9.21 | m |
| 13.1–13.5 | 6.76–6.56 | m |
| 17.8–18.4 | 4.98–4.82 | w–m |
| 20.8–21.3 | 4.27–4.17 | m–vs |
| 22.2–22.85 | 4.00–3.892 | m–vs |
| 26.4–27.05 | 3.376–3.296 | w–m |

TABLE Q

| 2θ | (BAPSO-40) d(Å) | Relative Intensity |
|---|---|---|
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| 2θ | (BAPSO-41) d(Å) | Relative Intensity |
|---|---|---|
| 13.6–13.8 | 6.51–6.42 | w–m |
| 21.1–21.3 | 4.21–4.17 | vs |
| 22.1–22.4 | 4.02–3.97 | m–s |
| 22.8–23.0 | 3.90–3.86 | m |
| 25.5–25.9 | 3.493–3.44 | w–m |

TABLE S

| 2θ | (BAPSO-42) d(Å) | Relative Intensity |
|---|---|---|
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

| 2θ | (BAPSO-43) d(Å) | Relative Intensity |
|---|---|---|
| 12.3–12.95 | 7.20–6.83 | m–vs |
| 16.8–17.45 | 5.28–5.09 | vw–w |
| 21.45–21.85 | 4.145–4.071 | m–vs |
| 27.1–27.85 | 3.291–3.232 | w–vs |
| 32.4–33.2 | 2.763–2.699 | vw–m |

TABLE U (BAPSO-44)

| 2θ | d(Å) | Relative Intensity |
|---|---|---|
| 9.2–9.6 | 9.61–9.21 | m–vs |
| 15.9–16.3 | 5.57–5.44 | vw–m |
| 20.5–21.0 | 4.33–4.23 | m–vs |
| 24.3–25.1 | 3.66–3.548 | w–m |
| 30.5–31.1 | 2.931–2.876 | vw–m |

TABLE V (BAPSO-46)

| 2θ | d(Å) | Relative Intensity |
|---|---|---|
| 7.2–8.1 | 12.28–10.92 | vs |
| 12.9–13.6 | 6.86–6.51 | vw |
| 21.2–22.2 | 4.19–4.501 | vw–m |
| 22.5–23.45 | 3.95–3.793 | vw–m |
| 26.6–27.9 | 3.351–3.198 | vw–m |

TABLE W (BAPSO-47)

| 2θ | d(Å) | Relative Intensity |
|---|---|---|
| 9.4–9.6 | 9.41–9.21 | vs |
| 12.8–13.1 | 6.92–6.76 | vw–m |
| 16.0–16.3 | 5.54–5.44 | vw–m |
| 20.5–21.0 | 4.31–4.23 | m–vs |
| 24.6–25.3 | 3.613–3.526 | vw–m |
| 30.6–31.1 | 2.921–2.876 | vw–m |

TABLE X (BAPSO-51)

| 2θ | d(Å) | Relative Intensity |
|---|---|---|
| 7.9–8.1 | 11.91–10.91 | w–s |
| 11.8–12.0 | 7.50–7.38 | m–vs |
| 13.7–13.9 | 6.46–6.37 | m–vs |
| 18.1–18.4 | 4.90–4.82 | w–s |
| 22.8–23.1 | 3.900–3.850 | w–vs |

The following examples are provided to further illustrate the invention and are not intended to be limiting thereof:

Example 1

(Preparation of BAPSO-5)

a) BAPSO-5 is prepared from a reaction mixture having a composition, expressed in terms of the molar oxide ratios of the components of the reaction mixture, of:

1.0–2.0 TPA : 0.05–0.2 $B_2O_3$: 0.5–1.0 $Al_2O_3$: 0.5–1.0 $P_2O_5$ : 0.1–0.6 $SiO_2$: 40–100 $H_2O$ where "TPA" denotes tripropylanine.

The reaction mixture is digested by placing the reaction mixture in a sealed stainless steel pressure vessel and heating it at an effective temperature and for an effective time to produce BAPSO-5 product. Solids are recovered by filtration, washed with water and dried in air at room temperature.

The BAPSO-5 product's chemical analysis shows the BAPSO-5 product contains boron, aluminum, phosphorus and silicon in amounts within the pentagonal compositional area defined by points A, B, C, D and E of FIG. 1.

The X-ray powder diffraction pattern of a BAPSO-5 product is characterized by the following data:

| 2θ | d(Å) | Relative Intensity |
|---|---|---|
| 7.2–7.7 | 12.28–11.48 | m–vs |
| 19.4–19.9 | 4.58–4.46 | w–m |
| 20.85–21.3 | 4.26–4.17 | w–vs |
| 22.1–22.6 | 4.02–3.93 | m–vs |

-continued

| 2θ | d(Å) | Relative Intensity |
|---|---|---|
| 25.6–26.1 | 3.480–3.414 | vw–m | b) The X-ray powder diffraction pattern for a calcined BAPSO-5 is also characterized by the X-ray pattern of part a).

c) When the calcined BAPSO-5 of part (b) is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter (Å) | Pressure (Torr) | Temp, °C. | Wt. % Adsorbed* |
|---|---|---|---|---|
| $O_2$ | 3.46 | 100 | −183 | 7 |
| $O_2$ | 3.46 | 750 | −183 | 10 |
| Neopentane | 6.2 | 700 | 24 | 4 |
| $H_2O$ | 2.65 | 4.3 | 24 | 4 |
| $H_2O$ | 2.65 | 20.0 | 24 | 12 |

*typical amount adsorbed

The pore diameter of BAPSO-5 is greater than about 6.2 Å.

Example 2

(Preparation of BAPSO-11)

a) BAPSO-11 is prepared from a reaction mixture having a composition, expressed in terms of the molar oxide ratios of the components of the reaction mixture, of:

1.0–2.0 DPA 0.05–0.2 $B_2O_3$: 0.5–1.0 $Al_2O_3$: 0.5–1.0 $P_2O_5$: 0.1–0.6 $SiO_2$: 40–100 $H_2O$ where "DPA" denotes di-n-propylamine.

The reaction mixture is digested by placing the reaction mixture in a sealed stainless steel pressure vessel and heating it at an effective temperature and for an effective time to produce BAPSO-11 product. Solids are then recovered by filtration, washed with water and dried in air at room temperature.

The BAPSO-11 product's chemical analysis shows the BAPSO-11 product contains boron, aluminum, phosphorus and silicon in amounts within the pentagonal compositional area defined by points A, B, C, D and E of FIG. 1.

The X-ray powder diffraction pattern of a BAPSO-11 product is characterized by the following data:

| 2θ | d(Å) | Relative Intensity |
|---|---|---|
| 7.8–8.2 | 11.19–10.85 | m–s |
| 9.2–9.8 | 9.83–9.03 | vw–vs |
| 12.8–13.6 | 6.92–6.51 | vw–m |
| 19.9–20.5 | 4.46–4.33 | m–s |
| 20.8–21.8 | 4.27–4.08 | m–vs |
| 22.0–22.6 | 4.04–3.93 | m–vs |
| 22.6–23.1 | 3.93–3.85 | vw–vs |
| 23.1–23.5 | 3.85–3.79 | w–vs | b) The X-ray powder diffraction pattern for a calcined BAPSO-11 is also characterized by the X-ray pattern of part a).

c) When the calcined BAPSO-11 of part (b) is utilized in adsorption capacity studies using a standard McBain-Bakr gravimetric adsorption apparatus the measurements are made on a sample after activation at 350° C.

in vacuum. The following data are used in the adsorption studies:

| Adsorbate | Kinetic Diameter (Å) | Pressure (Torr) | Temp, °C. | Wt. % Adsorbed* |
|---|---|---|---|---|
| $O_2$ | 3.46 | 100 | −183 | 5 |
| $O_2$ | 3.46 | 750 | −183 | 6 |
| Cyclohexane | 6.0 | 90 | 24 | 4 |
| $H_2O$ | 2.65 | 4.3 | 24 | 6 |
| $H_2O$ | 2.65 | 20 | 24 | 8 |

*typical amount adsorbed

The pore diameter of BAPSO-11 is about 6 Å.

Example 3

Preparation of BAPSO-17)

a) BAPSO-17 is prepared from a reaction mixture having a composition, expressed in terms of the molar oxide ratios of the components of the reaction mixture, of:

1.0–2.0 QN : 0.05–0.2 $B_2O_3$ : 0.5–1.0 $Al_2O_3$:
0.5–1.0 $P_2O_5$: 0.1–0.6 $SiO_2$: 40–100 $H_2O$ where "QN" denotes quinuclidine.

The reaction mixture is digested by placing the reaction mixture in a sealed stainless steel pressure vessel and heating it at an effective temperature and for an effective time to produce BAPSO-17 product. Solids are then recovered by filtration, washed with water and dried in air at room temperature.

The BAPSO-17 product's chemical analysis shows the BAPSO-17 product contains boron, aluminum, phosphorus and silicon in amounts within the pentagonal compositional area defined by points A, B, C, D and E of FIG. 1.

The X-ray powder diffraction pattern of a BAPSO-17 product is characterized by the following data:

| 2θ | d(Å) | Relative Intensity |
|---|---|---|
| 7.70–7.75 | 11.5–11.4 | vs |
| 13.4 | 6.61 | s-vs |
| 15.5–15.55 | 5.72–5.70 | s |
| 19.65–19.7 | 4.52–4.51 | w-s |
| 20.5–20.6 | 4.33–4.31 | vs |
| 31.8–32.0 | 2.812–2.797 | w-s | b) The X-ray powder diffraction pattern for a calcined BAPSO-17 is also characterized by the X-ray pattern of part a).

c) When the calcined BAPSO-17 of part (b) is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter (Å) | Pressure (Torr) | Temp, °C. | Wt. % Adsorbed* |
|---|---|---|---|---|
| $O_2$ | 3.46 | 100 | −183 | 10 |
| $O_2$ | 3.46 | 750 | −183 | 12 |
| n-butane | 4.3 | 100 | 24 | 4 |
| $H_2O$ | 2.65 | 4.3 | 24 | 13 |
| $H_2O$ | 2.65 | 20 | 24 | 14 |

*typical amount adsorbed

The pore diameter of BAPSO-17 is about 4.3 Å.

Example 4

(Preparation of BAPSO-31)

a) BAPSO-31 is prepared from a reaction mixture having a composition, expressed in terms of the molar oxide ratios of the components of the reaction mixture, of:

1.0–2.0 DPA : 0.05–0.2 $B_2O_3$: 0.5–1.0 $Al_2O_3$:
0.5–1.0 $P_2O_5$: 0.1–0.6 $SiO_2$: 40–100 $H_2O$ where "DPA" denotes di-n-propylamine.

The reaction mixture is seeded with crystals of AlPO$_4$-31 (U.S. Pat. No. 4,310,440) and digested by placing the reaction mixture in a sealed stainless steel pressure vessel and heating it at an effective temperature and for an effective time to produce BAPSO-31 product. Solids are then recovered by filtration, washed with water and dried in air at room temperature.

The BAPSO-31 product's chemical analysis shows the BAPSO-31 product contains boron, aluminum, phosphorus and silicon in amounts within the pentagonal compositional area defined by points A, B, C, D and E of FIG. 1.

The X-ray powder diffraction pattern of a BAPSO-31 product is characterized by the following data:

| 2θ | d(Å) | Relative Intensity |
|---|---|---|
| 8.4–9.5 | 10.53–9.31 | w-s |
| 20.2–20.4 | 4.40–4.35 | m |
| 22.0–22.1 | 4.040–4.022 | m |
| 22.5–22.7 | 3.952–3.92 | vs |
| 31.6–31.8 | 2.831–2.814 | w-m | b) The X-ray powder diffraction pattern for a calcined BAPSO-31 is also characterized by the X-ray pattern of part a).

c) When the calcined BAPSO-31 of part (b) is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter (Å) | Pressure (Torr) | Temp, °C. | Wt. % Adsorbed* |
|---|---|---|---|---|
| $O_2$ | 3.46 | 100 | −183 | 4 |
| $O_2$ | 3.46 | 750 | −183 | 6 |
| Cyclohexane | 6.0 | 90 | 24 | 3 |
| Neopentane | 6.2 | 700 | 24 | 3 |
| $H_2O$ | 2.65 | 4.3 | 24 | 3 |
| $H_2O$ | 2.65 | 20 | 24 | 10 |

*typical amount adsorbed

The pore diameter of BAPSO-31 is greater than about 6.2 Å.

Example 5

(Preparation of BAPSO-34)

a) A reaction mixture was prepared in two stages. In the first stage, 83.3 grams of aluminum isopropoxide were added to 400 ml. of isopropanol and the resultant mixture was refluxed with stirring for 1 hour; to the resultant mixture were added 46.1 grams of 85 wt. percent orthophosphoric acid ($H_3PO_4$) A solid precipitated and was recovered by filtration, washed with water and dried at ambient temperature. In the second stage, 7 1 grams of the solid produced in the first stage was added to 11.3 grams of water, and to the resultant mixture were added 4.1 grams of trimethylborate and then a dispersion of 0.5 gram of fumed silica (95 wt. percent $SiO_2$, 5 wt. percent $H_2O$) in 7.3 grams of 40 wt. percent aqueous tetraethylammonium hydroxide ($Et_4NOH$). Finally, there were added to the resultant mixture 3.1 grams of di-n-propylamine ($Pr_2NH$), and the mixture was stirred until homogeneous. The composition of the final reaction mixture thus produced, expressed in terms of the molar oxide ratios of the components of the reaction mixture, was:

1.0 $(Et_4N)_2O$ : 1.5 $Pr_2NH$ : 1.0 $B_2O_3$: 1.0 $Al_2O_3$:
0.4 $SiO_2$: 1.0 $P_2O_5$: 50 $H_2O$ : 6.0 MeOH.

This final reaction mixture was digested by sealing it in a stainless steel pressure vessel lined with polytetrafluoroethylene and heating it in an oven at 150° C. under autogeneous pressure for 72 hours. The solid reaction product (which was determined by the analyses described below to be SAPSO-34) was recovered by filtration, washed with water and dried in air at ambient temperature.

A sample of this solid reaction product was analyzed and the following chemical analysis obtained:

| Component | Weight percent |
|---|---|
| Carbon | 10.5 |
| $B_2O_3$ | 1.9 |
| $Al_2O_3$ | 32.9 |
| $SiO_2$ | 5.8 |
| $P_2O_5$ | 35.8 |
| LOI* | 15.2 |

*LOI indicates loss on ignition.

The above chemical analysis corresponds to a product composition in molar oxide ratios of:

0.17 $(Et_4N)_2O$ : 0.08 $B_2O_3$: 1.0 $Al_2O_3$:
0.30 $SiO_2$: 0.78 $P_2O_5$: 1.4 $H_2O$, which corresponds to an empirical composition, on an anhydrous basis, of:

0.042 $(Et_4N)_2O$ : $(Al_{0.496}P_{0.387}Si_{0.074}B_{0.042})O_2$.

Thus, the product contained boron, aluminum, silicon and phosphorus in amounts within the pentagonal compositional area defined by points A, B, C, D and E of FIG. 1.

The X-ray powder diffraction pattern of the product, as synthesized, was characterized by the data in the following Table LA. (Hereinafter, Tables designated AA, AB etc. are Tables of X-ray data which include all the peaks mentioned in Table A above, and similarly for Tables designated LA etc.):

TABLE LA (BAPSO-34)

| $2\theta$ | d(Å) | Relative Intensity $100 \times I/I_o$ |
|---|---|---|
| 9.5 | 9.27 | 100 |
| 12.9 | 6.85 | 7 |
| 14.1 | 6.29 | 6 |
| 16.0 | 5.52 | 34 |
| 17.8 | 4.98 | 5 |
| 20.6 | 4.30 | 49 |
| 21.5 | 4.14 | 7 |
| 23.1 | 3.85 | 3 |
| 25.2 | 3.53 | 10 |
| 25.9 | 3.44 | 11 |
| 29.7 | 3.009 | 4 |
| 30.7 | 2.916 | 17 |
| 31.2 | 2.867 | 13 |

Example 6

(Preparation of BAPSO-44)

a) BAPSO-44 is prepared from a reaction mixture having a composition, expressed in terms of the molar oxide ratios of the components of the reaction mixture, of:

1.0–2.0 CHA : 0.05–0.2 $B_2O_3$: 0.5–1.0 $Al_2O_3$:
0.5–1.0 $P_2O_5$: 0.1–0.6 $SiO_2$: 40–100 $H_2O$ where "CHA" denotes cyclohexylamine.

The reaction mixture is digested by placing the reaction mixture in a sealed stainless steel pressure vessel and heating it at an effective temperature and for an effective time to produce BAPSO-44 product. Solids are then recovered by filtration, Washed with water and dried in air at room temperature.

The BAPSO-44 product's chemical analysis shows the BAPSO-44 product contains boron, aluminum, phosphorus and silicon in amounts within the pentagonal compositional area defined by points A, B, C, D and E of FIG. 1.

The X-ray powder diffraction pattern of a BAPSO-44 product is characterized by the following data:

| $2\theta$ | d(Å) | Relative Intensity |
|---|---|---|
| 9.2–9.6 | 9.61–9.21 | m-vs |
| 15.9–16.3 | 5.57–5.44 | vw-m |
| 20.5–21.0 | 4.33–4.23 | m-vs |
| 24.3–25.1 | 3.66–3.548 | w-m |
| 30.5–31.1 | 2.931–2.876 | vw-m | b) When the calcined BAPSO-44 is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter (Å) | Pressure (Torr) | Temp, °C. | Wt. % Adsorbed* |
|---|---|---|---|---|
| $O_2$ | 3.46 | 100 | −183 | 13 |
| $O_2$ | 3.46 | 750 | −183 | 16 |
| n-hexane | 4.3 | 100 | 24 | 2 |
| $H_2O$ | 2.65 | 4.3 | 24 | 15 |
| $H_2O$ | 2.65 | 20 | 24 | 17 |

*typical amount adsorbed

The pore diameter of BAPSO-44 is about 4.3A.

Example 7

(Preparation of BAPSO-35)

a) To prepare BAPSO-35, a reaction mixture was formed by combining 39.4 grams of aluminum tri-sec-butoxide ($Al(OC_4H_9)_3$) with 10.4 grams of tetraethyl orthosilicate and 23.1 grams of 25% methanolic tetraethylammonium hydroxide, and adding to the resultant mixture 20.8 grams of trimethyl borate. 11.5 grams of 85 wt. percent orthophosphoric acid ($H_3PO_4$) mixed with 9.2 grams of water were then added gradually with stirring until the mixture was homogeneous. The composition of the final reaction mixture thus produced, expressed in terms of the molar oxide ratios of the components of the reation mixture, was:

1.0 $(Et_4N)_2O$ : 1.0 $B_2O_3$: 0.8 $Al_2O_3$:
0.5 $SiO_2$: 1.0 $P_2O_5$: 10 $H_2O$ : 40.4 ROH*. * =4.8 butanol, 33.6 methanol and 2.0 ethanol A portion of this final reaction mixture was digested by sealing it in a stainless steel pressure vessel lined with polytetrafluoroethylene and heating it in an oven at 200° C. under autogeneous pressure for 168 hours. The solid reaction product was recovered by filtration, washed with water and dried in air at 100° C.

A sample of this solid reaction product was analyzed and the following chemical analysis obtained:

| Component | Weight percent |
|---|---|
| Carbon | 10.5 |
| Nitrogen | 2.0 |
| $B_2O_3$ | 1.5 |
| $Al_2O_3$ | 28.0 |
| $SiO_2$ | 12.6 |
| $P_2O_5$ | 39.7 |
| LOI* | 19.6 |

*LOI indicates loss on ignition.

The above chemical analysis corresponds to a product composition in molar oxide ratios of:
0.26 $(Et_4N)_2O$ 0.08 $B_2O_3$: 1.0 $Al_2O_3$:
0.76 $SiO_2$: 1.02 $P_2O_5$: 0.91 $H_2O$
which corresponds to an empirical chemical composition, on an anhydrous basis, of:
0.052 $(Et_4N)_2O$: $(Al_{0.403}P_{0.411}Si_{0.154}B_{0.032})O_2$.
Thus, the product contained boron, aluminum, silicon and phosphorus in amounts within the pentagonal compositional area defined by points A, B, C, D and E of FIG. 1.

The X-ray powder diffraction pattern of the product, as synthesized, was characterized by the data in the following Table MA:

TABLE MA (BAPSO-35)

| 2θ | d(Å) | Relative Intensity 100 × I/I$_o$ |
|---|---|---|
| 8.7 | 10.16 | 27 |
| 11.0 | 8.03 | 69 |
| 13.5 | 6.57 | 43 |
| 16.1 | 5.52 | 7 |
| 17.4 | 5.09 | 73 |
| 17.9 | 4.96 | 13 |
| 21.1 | 4.22 | 58 |
| 22.1 | 4.02 | 100 |
| 22.9 | 3.89 | 8 |
| 23.5 | 3.79 | 33 |
| 24.5 | 3.64 | 8 |
| 25.1 | 3.55 | 7 |
| 27.1 | 3.287 | 19 |
| 28.6 | 3.120 | 45 |
| 29.3 | 3.045 | 7 |
| 31.8 | 2.818 | 8 |
| 32.4 | 2.762 | 42 |
| 34.6 | 2.590 | 12 |

The X-ray powder diffraction pattern of the product, after calcination at 600° C. for 1 hour, was characterized by the data in the following Table MB (the calcined product displayed additional peaks indicating the presence of a minor amount of BAPSO-51 (see Example 9 below) impurity, but these impurity peaks are omitted for simplicity):

TABLE MB (BAPSO-35)

| 2θ | d(Å) | Relative Intensity 100 × I/I$_o$ |
|---|---|---|
| 8.8 | 10.04 | 19 |
| 11.1 | 7.96 | 94 |
| 13.7 | 6.48 | 100 |
| 16.3 | 5.45 | 5 |
| 17.6 | 5.04 | 33 |
| 21.1 | 4.20 | 33 |
| 22.3 | 3.98 | 64 |
| 23.1 | 3.84 | 5 |
| 23.7 | 3.75 | 19 |
| 24.6 | 3.62 | 5 |
| 25.2 | 3.53 | 15 |
| 27.5 | 3.25 | 26 |
| 28.7 | 3.11 | 44 |
| 29.7 | 3.01 | 12 |
| 31.9 | 2.809 | 7 |
| 32.8 | 2.730 | 31 |
| 34.8 | 2.580 | 8 | b) A sample of the calcined product produced in part (a) was subjected to adsorption capacity studies using a standard McBain-Bakr gravimetric adsorption apparatus. The following data were generated in the adsorption studies:

| Adsorbate | Kinetic Diameter (Å) | Pressure (Torr) | Temp, °C. | Wt. % Adsorbed* |
|---|---|---|---|---|
| $O_2$ | 3.46 | 100 | −183 | 19.0 |
| $O_2$ | 3.46 | 750 | −183 | 24.2 |
| n-Hexane | 4.3 | 45 | 22.7 | 9.7 |
| $H_2O$ | 2.65 | 4.6 | 21.3 | 23.8 |
| $H_2O$ | 2.65 | 20 | 22.3 | 38.4 |
| Neopentane | 6.2 | 100 | 21.4 | 0.5 |

From the above data, the pore size of the calcined product was determined to be greater than about 346 Å, as shown by the adsorption of oxygen (kinetic diameter of 3.46 Å) and less than about 6.2 Å, as shown by the low adsorption of neopentane (kinetic diameter of 6.2 Å).

EXAMPLE 8 (Preparation of BAPSO-41)

To prepare BAPPSO-41, a reaction mixture was formed by combining 6.9 grams of 85 wt. percent orthophosphoric acid ($H_3PO_4$) with 8.7 grams of water, and adding to the resultant mixture 6.9 grams of hydrated aluminum oxide in the form of a pseudo-boehmite phase comprising 74.2 wt. percent of $Al_2O_3$ and 25.8 wt. percent of $H_2O$. The resultant mixture was stirred until homogeneous. To this homogeneous mixture was added 1.3 grams of fumed silica (95 wt. percent $SiO_2$, 5 wt. percent $H_2O$) dispersed in a solution of 12.4 grams of boric acid ($H_3BO_3$) in 103.5 grams of 25 wt. percent methanolic tetrabutylammonium hydroxide ($Bu_4NOH$), the mixture being stirred until homogeneous. The composition of the final reaction mixture thus produced, expressed in terms of the molar oxide ratios of the components of the reaction mixture, was:
1.0 $(Bu_4N)_2O$ : 2.0 $B_2O_3$:1.0 $Al_2O_3$:
0.4 $SiO_2$: 1.0 $P_2O_5$: 13.7 $H_2O$ : 48.5 MeOH.

A portion of this final reaction mixture was digested by sealing it in a stainless steel pressure vessel lined with polytetrafluoroethylene and heating it in an oven at 200° C. under autogeneous pressure for 96 hours. The solid reaction product was recovered by filtration, washed with water and dried in air at ambient temperature.

A sample of this solid reaction product was analyzed and the following chemical analysis obtained:

| Component | Weight percent |
| --- | --- |
| Carbon | 5.5 |
| Nitrogen | 0.62 |
| $B_2O_3$ | 1.9 |
| $Al_2O_3$ | 32.9 |
| $SiO_2$ | 5.2 |
| $P_2O_5$ | 43.5 |
| LOI* | 15.2 |

*LOI indicates loss on ignition.

The above chemical analysis corresponds to a product composition in molar oxide ratios of:

0.07 $(Bu_4N)_2O$: 0.07 $B_2O_3$: 1.0 $Al_2O_3$:
0.27 $SiO_2$ : 0.95 $P_2O_5$: 0.69 $H_2O$ which corresponds to an empirical chemical composition, on an anhydrous basis, of:

0.016 $(Bu_4N)_2O$: $(Al_{0.464}P_{0.441}Si_{0.062}B_{0.033})O_2$.

Thus, the product contained boron, aluminum, silicon and phosphorus in amounts within the pentagonal compositional area defined by points A, B, C, D and E of FIG. 1.

The X-ray powder diffraction pattern of the product, as synthesized, was characterized by the data in the following Table RA:

TABLE RA (BAPSO-41)

| $2\theta$ | d(Å) | Relative Intensity $100 \times I/I_o$ |
| --- | --- | --- |
| 6.5 | 13.60 | 15 |
| 9.7 | 9.31 | 30 |
| 13.7 | 6.46 | 20 |
| 18.3 | 4.85 | 14 |
| 21.3 | 4.17 | 100 |
| 22.3 | 3.97 | 65 |
| 23.0 | 3.87 | 35 |
| 25.5 | 3.493 | 15 |
| 25.7 | 3.466 | 14 |
| 29.5 | 3.028 | 20 |
| 31.4 | 2.849 | 5 |
| 33.4 | 2.683 | 4 |
| 36.7 | 2.449 | 2 |
| 37.8 | 2.380 | 7 |
| 38.4 | 2.344 | 2 |
| 39.8 | 2.265 | 2 |
| 43.2 | 2.094 | 2 |
| 51.7 | 1.768 | 2 |

A comparison of this X-ray Table with that of the corresponding silicon-aluminum-phosphorus oxide, SAPO-41 (see U.S. Pat. No. 4,440,871 Example 54, Table HH) shows that BAPSO-41 has slightly smaller d-spacings consistent with replacement of some of the aluminum atoms in the framework by smaller boron atoms.

EXAMPLE 9 (Preparation of BAPSO-51)

a) To prepare BAPSO-51, a reaction mixture was formed by combining 60 rams of aluminum hexade coxide ($Al(OC_{16}H_{33})_3$) with 5.2 grams of tetraethyl orthosilicate and 59.0 grams of 25% methanolic tetraethylammonium hydroxide, and adding to the resultant mixture 10.4 grams of trimethyl borate. 11.5 grams of 85 wt. percent orthophosphoric acid ($H_3PO_4$) were then added gradually with stirring, then 4.6 grams of water were added and the resulting solution mixed for 5 minutes. The composition of the final reaction mixture thus produced, expressed in terms of the molar oxide ratios of the components of the reaction mixture, was:

1.0 $(Et_4N)_2O$ :1.0 $B_2O_3$: 0.8 $Al_2O_3$:
0.5 $SiO_2$: 1.0 $P_2O_5$: $10H_2O$ : 40.4 ROH*. * =4.8 hexadecanol, 33.6 methanol and 2.0 ethanol Two portions of this final reaction mixture were digested by sealing them in stainless steel pressure vessels lined with polytetrafluoroethylene and heating them in an oven at 200° C. under autogeneous pressure for 168 hours. The solid reaction products were recovered by filtration, washed with water or acetone respectively and dried in air at 100° C.

Samples of both the water-washed and the acetone-washed solid reaction products were analyzed and the following chemical analyses obtained:

| Component | Water-washed Weight percent | Acetone-washed Weight percent |
| --- | --- | --- |
| Carbon | 24.5 | 21.7 |
| Nitrogen | 1.7 | 1.9 |
| $B_2O_3$ | 1.0 | 5.8 |
| $Al_2O_3$ | 25.5 | 20.6 |
| $SiO_2$ | 10.8 | 8.5 |
| $P_2O_5$ | 38.0 | 31.8 |
| LOI* | 24.1 | 34.9 |

*LOI indicates loss on ignition.

product compositions in molar oxide ratios of:

Water-washed
0.31 $(Et_4N)_2O$:0.06 $B_2O_3$:
1.0 $Al_2O_3$:0.72 $SiO_2$:1.07 $P_2O_5$:
0.56 $H_2O$ Acetone-washed
0.32 $(Et_4N)_2O$:0.41 $B_2O_3$:
1.0 $Al_2O_3$:0.70 $SiO_2$:1.11 $P_2O_5$:
0.99 $H_2O$ which correspond to empirical chemical compositions, on an anhydrous basis, of :

Water-washed
0.062 $(Et_4N)_2O$:$(Al_{0.402}P_{0.430}Si_{0.144}B_{0.024})O_2$.

Acetone-washed
0.055 $(Et_4N)_2O$:$(Al_{0.348}P_{0.387}Si_{0.122}B_{0.143})O_2$.

Thus, the products contained boron, aluminum, silicon and phosphorus in amounts within the pentagonal compositional area defined by points A, B, C, D and E of FIG. 1.

The X-ray powder diffraction patterns of the products, as synthesized, were characterized by the data in the following Tables XA and XB (the products displayed additional peaks indicating the presence of minor amounts of BAPSO-34 and BAPSO-35 impurities (see Examples 5 and 7 respectively above), but these impurity peaks are omitted for simplicity:

TABLE XA (BAPSO-51, Water-washed)

| $2\theta$ | d(Å) | Relative Intensity $100 \times I/I_o$ |
| --- | --- | --- |
| 8.1 | 10.97 | 55 |
| 9.3 | 9.53 | 14 |
| 11.9 | 7.42 | 46 |
| 13.9 | 6.38 | 53 |
| 18.3 | 4.85 | 72 |
| 19.4 | 4.58 | 44 |
| 21.2 | 4.19 | 43 |
| 23.0 | 3.87 | 100 |
| 24.1 | 3.70 | 32 |
| 27.7 | 3.22 | 61 |

TABLE XA-continued
(BAPSO-51, Water-washed)

| 2θ | d(Å) | Relative Intensity 100 × I/I₀ |
|---|---|---|
| 33.4 | 2.68 | 36 |

TABLE XB
(BAPSO-51, Acetone-washed)

| 2θ | d(Å) | Relative Intensity 100 × I/I₀ |
|---|---|---|
| 8.0 | 11.09 | 49 |
| 9.3 | 9.56 | 10 |
| 11.8 | 7.48 | 44 |
| 13.8 | 6.42 | 48 |
| 18.2 | 4.88 | 73 |
| 19.3 | 4.61 | 48 |
| 21.1 | 4.21 | 36 |
| 22.9 | 3.89 | 100 |
| 24.0 | 3.71 | 30 |
| 27.6 | 3.23 | 56 |
| 33.3 | 2.69 | 30 |

The X-ray powder diffraction patterns of the products, after calcination at 600° C. for 1 hour, were characterized by the data in the following Tables XC and XD:

TABLE XC
(BAPSO-51, Water-washed)

| 2θ | d(Å) | Relative Intensity 100 × I/I₀ |
|---|---|---|
| 8.1 | 10.97 | 21 |
| 9.3 | 9.53 | 14 |
| 12.0 | 7.40 | 94 |
| 13.9 | 6.38 | 100 |
| 18.3 | 4.85 | 28 |
| 19.4 | 4.58 | 18 |
| 21.2 | 4.19 | 17 |
| 23.0 | 3.87 | 29 |
| 23.9 | 3.73 | 25 |
| 27.7 | 3.22 | 40 |

TABLE XD
(BAPSO-51, Acetone-washed)

| 2θ | d(Å) | Relative Intensity 100 × I/I₀ |
|---|---|---|
| 8.0 | 11.09 | 23 |
| 9.3 | 9.56 | 13 |
| 11.8 | 7.48 | 100 |
| 13.8 | 6.42 | 93 |
| 18.2 | 4.88 | 36 |
| 19.3 | 4.61 | 24 |
| 21.1 | 4.21 | 16 |
| 22.9 | 3.89 | 32 |
| 23.8 | 3.73 | 22 |
| 27.6 | 3.23 | 42 |
| 33.4 | 2.68 | 7 | b) Samples of the products produced in part (a) were calcined and subjected to absorption capacity studies using a standard McBain-Bakr gravimetric adsorption apparatus. The following data were generated in the adsorption studies:

| Adsorbate | Kinetic Diameter (Å) | Pressure (Torr) | Temp, °C. | Wt. % Adsorbed WW* | AW* |
|---|---|---|---|---|---|
| $O_2$ | 3.46 | 100 | −183 | 16.8 | 12.4 |
| $O_2$ | 3.46 | 750 | −183 | 21.6 | 15.7 |
| n-Hexane | 4.3 | 45 | 22.5 | 5.9 | 1.2 |
| iso-Butane | 5.0 | 102 | 23.2 | 0.6 | 0.1 |
| Xe | 3.96 | 100 | 22.0 | 7.2 | 5.2 |
| $H_2O$ | 2.65 | 4.6 | 22.6 | 24.4 | 23.2 |
| $H_2O$ | 2.65 | 19.0 | 21.8 | 33.3 | 32.8 |

*WW = water-washed, AW = acetone washed

From the above data, the pore size of the calcined product was determined to be near or greater than about 4.3 Å, as shown by the adsorption of n-hexane (kinetic diameter of 4.3 Å) and less than about 5.0 Å, as shown by the low adsorption of iso-butane (kinetic diameter of 5.0 Å).

PROCESS APPLICATIONS

The BAPSO compositions of the present invention are, in general, hydrophilic and adsorb water preferentially over common hydrocarbon molecules such as paraffins, olefins and aromatic species, e.g., benzene, xylenes and cumene. Thus the present molecular sieve compositions as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These BAPSOS are therefore suitably employed in the drying of reformer hydrogen streams and in the drying of oxygen, nitrogen or air prior to liquifaction.

The present BAPSO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art (for example, ion-exchange) and used, for example, in fabricating catalyst compositions having silica or alumina bases. Of the general class, those species having pores larger than about 4Å are preferred for catalytic applications.

Among the hydrocarbon conversion reactions catalyzed by BAPSO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using BAPSO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. (204° C. to 441° C.) using molar ratios of hydrogen to hydrocarbon in the range of between 2 and 80, pressures between 10 and 3500 p.s.i.g. (0.171 to 24.23 MPa.), and a liquid hourly space velocity (LHSV) of from 0.1 to 20, preferably 1.0 to 10.

The BAPSO catalyst compositions employed in hydrocracking are also suitable for use in reforming processes in which the hydrocarbon feedstocks contact the catalyst at temperatures of from about 700° F. to 1000° F. (371° C. to 538° C.), hydrogen pressures of from 100 to 500 p.s.i.g. (0 791 to 3.448 MPa.), LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerization processes in which feedstocks such as normal paraffins are converted to saturated branched chain isomers. Hydroisomerization is carried out at a temperature of from about 200° F. to 600° F. (93° C. to 316° C.), preferably 300° F. to 550° F. (149° C. to 288° C.) with an LHSV value of from about 0.2 to 1.0. Hydrogen (H) is supplied to the reactor in admixture with the hydrocarbon (Hc) feedstock in molar proportions (H/Hc) of between 1 and 5.

At somewhat higher temperatures, i.e. from about 650° F. to 1000° F. (343° C. to 538° C.), preferably 850° F. to 950° F. (454° C. to 510° C.) and usually at somewhat lower pressures within the range of about 15 to 50 p.s.i.g. (205 to 446 KPa.), the same catalyst compositions are used to hydroisomerize normal paraffins. Preferably the paraffin feedstock comprises normal paraffins having a carbon number range of $C_7$-$C_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The unique crystal structure of the present BAPSO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-percent of the overall composition. Extraneous hydrogen can, but need not, be present in the reaction zone which is maintained at a temperature of from about 400° to 750° F. (204° to 399° C.), pressures in the range of 100 to 2000 p.s.i.g. (0.791 to 13.89 MPa.) and LHSV values in the range of 0.1 to 15.

Catalytic cracking processes are preferably carried out with BAPSO compositions using feedstocks such as gas oils, heavy naphthas, deasphalted crude oil residua, etc., with gasoline being the principal desired product. Temperature conditions of 850° to 1100° F. (454° to 593° C.), LHSV values of 0.5 to 10 and pressure conditions of from about 0 to 50 p.s.i.g. (101 to 446 KPa.) are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the BAPSO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°-1000° F. (427°-538° C.) are employed at moderate hydrogen pressures of about 300-1000 p.s.i.g. (2.17-6.895 MPa.), other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like. Any of these may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed than with a feed containing less organonitrogen compounds. Consequently, the conditions under which denitrogenation, desulfurization and/or hydrocracking can be most expeditiously accomplished in any given situation are necessarily determined in view of the characteristics of the feedstocks, in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°-900° F. (260°-482° C.), while paraffins, naphthenes and alkyl aromatics are isomerized at temperatures of 700°-1000° F. (371°-538° C.). Particularly desirable isomerization reactions contemplated herein include the conversion of n-heptene and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexane to isohexene, cyclohexene to methylcyclopentene etc. The preferred form of the catalyst is a combination of the BAPSO with polyvalent metal compounds (such as sulfides) of metals of Group II-A, Group II-B and rare earth metals. For alkylation and dealkylation processes the BAPSO compositions having pores of at least 5A are preferred. When employed for dealkylation of alkyl aromatics, the temperature is usually at least 350° F.

(177° C.) and ranges up to a temperature at which substantial cracking of the feedstock or conversion products occurs, generally up to about 700° F. (371° C.). The temperature is preferably at least 450° F. (232° C.) and not greater than the critical temperature of the compound undergoing dealkylation. Pressure conditions are applied to retain at least the aromatic feed in the liquid state. For alkylation the temperature can be as low as 250° F. (121° C.) but is preferably at least 350° F. (177° C.). In the alkylation of benzene, toluene and xylene, the preferred alkylating agents are olefins such as ethylene and propylene.

We claim:

1. Crystalline molecular sieves comprising three-dimensional microporous framework structures of $BO_2$, $AlO_2$, $PO_2$ and $SiO_2$ tetrahedral units having an empirical chemical composition on an anhydrous basis expressed by the formula:

$$mR : (B_wAl_xP_ySi_z)O_2$$

wherein "R" represents at least one organic templating agent present in the intracrystalline pore system; "m" represents the molar amount of "R" present per mole of $(B_wAl_xP_ySi_z)O_2$ and has a value of zero to about 0.3; and "w", "x", "y" and "z" represent the mole fractions of boron, aluminum, phosphorus and silicon, respectively, present as tetrahedral oxides, said mole fractions being such that they are within the pentagonal compositional area defined by points A, B, C, D, and E of FIG. 1, said crystalline molecular sieves having a characteristic X-ray powder diffraction pattern which contains at least the d-spacings set forth in one of the following Tables C, F, J, N, P, T, V, W and X:

TABLE C

| | (BAPSO-14) | |
|---|---|---|
| 2θ | d (Å) | Relative Intensity |
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE F

| | (BAPSO-18) | |
|---|---|---|
| 2θ | d (Å) | Relative Intensity |
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE J*

| | (BAPSO-33) | |
|---|---|---|
| 2θ | d (Å) | Relative Intensity |
| 9.25–9.55 | 9.56–9.26 | w-m |
| 12.5–12.9 | 7.08–6.86 | vs |
| 16.9–17.3 | 5.25–5.13 | w-m |
| 20.45–20.9 | 4.34–4.25 | w-m |
| 23.85–24.25 | 3.73–3.67 | w-m |
| 26.05–26.35 | 3.42–3.38 | w-m |
| 27.3–27.6 | 3.27–3.23 | vs |

*as-synthesized form

TABLE N

| | (BAPSO-36) | |
|---|---|---|
| 2θ | d (Å) | Relative Intensity |
| 7.45–8.0 | 11.14–11.05 | vs |
| 8.1–8.3 | 10.91–10.65 | w-m |
| 16.3–16.6 | 5.44–5.34 | w-m |
| 18.9–19.4 | 4.70–4.57 | w-m |
| 20.7–21.0 | 4.29–4.23 | w-m |

TABLE P

| | (BAPSO-39) | |
|---|---|---|
| 2θ | d (Å) | Relative Intensity |
| 9.2–9.6 | 9.61–9.21 | m |
| 13.1–13.5 | 6.76–6.56 | m |
| 17.8–18.4 | 4.98–4.82 | w-m |
| 20.8–21.3 | 4.27–4.17 | m-vs |
| 22.2–22.85 | 4.00–3.892 | m-vs |
| 26.4–27.05 | 3.376–3.296 | w-m |

TABLE T

| | (BAPSO-43) | |
|---|---|---|
| 2θ | d (Å) | Relative Intensity |
| 12.3–12.95 | 7.20–6.83 | m-vs |
| 16.8–17.45 | 5.28–5.09 | vw-w |
| 21.45–21.85 | 4.145–4.071 | m-vs |
| 27.1–27.85 | 3.291–3.232 | w-vs |
| 32.4–33.2 | 2.763–2.699 | vw-m |

TABLE V

| | (BAPSO-46) | |
|---|---|---|
| 2θ | d (Å) | Relative Intensity |
| 7.2–8.1 | 12.28–10.92 | vs |
| 12.9–13.6 | 6.86–6.51 | vw |
| 21.2–22.2 | 4.19–4.501 | vw-m |
| 22.5–23.45 | 3.95–3.793 | vw-m |
| 26.5–27.9 | 3.351–3.198 | vw-m |

TABLE W

| | (BAPSO-47) | |
|---|---|---|
| 2θ | d (Å) | Relative Intensity |
| 9.4–9.6 | 9.41–9.21 | vs |
| 12.8–13.1 | 6.92–6.76 | vw-m |
| 16.0–16.3 | 5.54–5.44 | vw-m |
| 20.5–21.0 | 4.31–4.23 | m-vs |
| 24.6–25.3 | 3.613–3.526 | vw-m |
| 30.6–31.1 | 2.921–2.876 | vw-m |

TABLE X

| | (BAPSO-51) | |
|---|---|---|
| 2θ | d (Å) | Relative Intensity |
| 7.9–8.1 | 11.91–10.91 | w-s |
| 11.8–12.0 | 7.50–7.38 | m-vs |
| 13.7–13.9 | 6.46–6.37 | m-vs |
| 18.1–18.4 | 4.90–4.82 | w-s |
| 22.8–23.1 | 3.900–3.850 | v-vs. |

2. Crystalline molecular sieves according to claim 1 wherein the mole fractions of boron, aluminum, phosphorus and silicon present as tetrahedral oxides are within the hexagonal compositional area defined by points a, b, c, d, e and f of FIG. 2.

3. Crystalline molecular sieves according to claim 2 wherein the mole fractions of boron, aluminum, phosphorus and silicon present as tetrahedral oxides are within the hexagonal compositional area defined by points g, h, i, j, k and l of FIG. 2.

4. The crystalline molecular sieves of claim 1 wherein "m" is not greater than about 0.15.

5. The crystalline molecular sieves of claim 1 or 2 having a characteristic X-ray powder diffraction pattern which contains at least the d-spacings set forth in Table C given in claim 1.

6. The crystalline molecular sieves of claim 1 or 2 having a characteristic X-ray powder diffraction pattern which contains at least the d-spacings set forth in Table F given in claim 1.

7. The crystalline molecular sieves of claim 1 or 2 having a characteristic X-ray powder diffraction pattern which contains at least the d-spacings set forth in Table J given in claim 1.

8. The crystalline molecular sieves of claim 1 or 2 having a characteristic X-ray powder diffraction pattern which contains at least the d-spacings set forth in Table P given in claim 1.

9. The crystalline molecular sieves of claim 1 or 2 having a characteristic X-ray powder diffraction pattern which contains at least the d-spacings set forth in Table T given in claim 1.

10. The crystalline molecular sieves of claim 1 or 2 having a characteristic X-ray powder diffraction pattern which contains at least the d-spacings set forth in Table V given in claim 1.

11. The crystalline molecular sieves of claim 1 or 2 having a characteristic X-ray powder diffraction pattern which contains at least the d-spacings set forth in Table W given in claim 1.

12. The crystalline molecular sieves of claim 1 or 2 having a characteristic X-ray powder diffraction pattern which contains at least the d-spacings set forth in Table X given in claim 1.

13. The crystalline molecular sieves of claim 12 wherein the X-ray powder diffraction pattern set forth in Table X contains at least the d-spacings set forth in one of the following Tables XA XB, SC and XD:

TABLE XA
(BAPSO-51)

| $2\theta$ | d(Å) | Relative Intensity $100 \times I/I_o$ |
|---|---|---|
| 8.1 | 10.97 | 55 |
| 9.3 | 9.53 | 14 |
| 11.9 | 7.42 | 46 |
| 13.9 | 6.38 | 53 |
| 18.3 | 4.85 | 72 |
| 19.4 | 4.58 | 44 |
| 21.2 | 4.19 | 43 |
| 23.0 | 3.87 | 100 |
| 24.1 | 3.70 | 32 |
| 27.7 | 3.22 | 61 |
| 33.4 | 2.68 | 36 |

TABLE XB
(BAPSO-51)

| $2\theta$ | d(Å) | Relative Intensity $100 \times I/I_o$ |
|---|---|---|
| 8.0 | 11.09 | 49 |
| 9.3 | 9.56 | 10 |
| 11.8 | 7.48 | 44 |
| 13.8 | 6.42 | 48 |
| 18.2 | 4.88 | 73 |
| 19.3 | 4.61 | 48 |
| 21.1 | 4.21 | 36 |
| 22.9 | 3.89 | 100 |
| 24.0 | 3.71 | 30 |
| 27.6 | 3.23 | 56 |
| 33.3 | 2.69 | 30 |

TABLE XC
(BAPSO-51)

| $2\theta$ | d(Å) | Relative Intensity $100 \times I/I_o$ |
|---|---|---|
| 8.1 | 10.97 | 21 |
| 9.3 | 9.53 | 14 |
| 12.0 | 7.40 | 94 |
| 13.9 | 6.38 | 100 |
| 18.3 | 4.85 | 28 |
| 19.4 | 4.58 | 18 |
| 21.2 | 4.19 | 17 |
| 23.0 | 3.87 | 29 |
| 23.9 | 3.73 | 29 |
| 27.7 | 3.22 | 40 |

TABLE XD
(BAPSO-51)

| $2\theta$ | d(Å) | Relative Intensity $100 \times I/I_o$ |
|---|---|---|
| 8.0 | 11.09 | 23 |
| 9.3 | 9.56 | 13 |
| 11.8 | 7.48 | 100 |
| 13.8 | 6.42 | 93 |
| 18.2 | 4.88 | 36 |
| 19.3 | 4.61 | 24 |
| 21.1 | 4.21 | 16 |
| 22.9 | 3.89 | 32 |
| 23.8 | 3.73 | 22 |
| 27.6 | 3.23 | 42 |
| 33.4 | 2.68 | 7. |

14. Process for preparing crystalline molecular sieves having three-dimensional microporous framework structures of $BO_2$, $AlO_2$, $PO_2$ and $SiO_2$ tetrahedral units having an empirical chemical composition on an anhydrous basis expressed by the formula:

$$mR : (B_wAl_xP_ySi_z)O_2$$

wherein "R" represents at least one organic templating agent present in the intracrystalline pore system; "m" represents the molar amount of "R" present per mole of $(B_wAl_xP_ySi_z)O_2$ and has a value of zero to about 0.3; and "w", "x", "y" and "z" represent the mole fractions of boron, aluminum, phosphorus and silicon, respectively, present as tetrahedral oxides, said mole fractions being such that they are within the pentagonal compositional area defined by points A, B, C, D, and E of FIG. 1, said crystalline molecular sieves having a characteristic X-ray powder diffraction pattern which contains at least the d-spacings set forth in one of the following Tables C, F, J, N, P, T, V, W and X:

TABLE C
(BAPSO-14)

| $2\theta$ | d (Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE F
(BAPSO-18)

| $2\theta$ | d (Å) | Relative Intensity |
|---|---|---|
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |

TABLE F-continued

| | (BAPSO-18) | |
|---|---|---|
| 2θ | d (Å) | Relative Intensity |
| 20.95–21.05 | 4.24–4.22 | m |
| 31.8–32.5 | 2.814–2.755 | m |

TABLE J*

| | (BAPSO-33) | |
|---|---|---|
| 2θ | d (Å) | Relative Intensity |
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K

| | *(BAPSO-33) | |
|---|---|---|
| 2θ | d (Å) | Relative Intensity |
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE N

| | (BAPSO-36) | |
|---|---|---|
| 2θ | d (Å) | Relative Intensity |
| 7.45–8.0 | 11.14–11.05 | vs |
| 8.1–8.3 | 10.91–10.65 | w–m |
| 16.3–16.6 | 5.44–5.34 | w–m |
| 18.9–19.4 | 4.70–4.57 | w–m |
| 20.7–21.0 | 4.29–4.23 | w–m |

TABLE P

| | (BAPSO-39) | |
|---|---|---|
| 2θ | d (Å) | Relative Intensity |
| 9.2–9.6 | 9.61–9.21 | m |
| 13.1–13.5 | 6.76–6.56 | m |
| 17.8–18.4 | 4.98–4.82 | w–m |
| 20.8–21.3 | 4.27–4.17 | m–vs |
| 22.2–22.85 | 4.00–3.892 | m–vs |
| 26.4–27.05 | 3.376–3.296 | w–m |

TABLE T

| | (BAPSO-43) | |
|---|---|---|
| 2θ | d (Å) | Relative Intensity |
| 12.3–12.95 | 7.20–6.83 | m–vs |
| 16.8–17.45 | 5.28–5.09 | vw–w |
| 21.45–21.85 | 4.145–4.071 | m–vs |
| 27.1–27.85 | 3.291–3.232 | w–vs |
| 32.4–33.2 | 2.763–2.699 | vw–m |

TABLE V

| | (BAPSO-46) | |
|---|---|---|
| 2θ | d (Å) | Relative Intensity |
| 7.2–8.1 | 12.28–10.92 | vs |
| 12.9–13.6 | 6.86–6.51 | vw |
| 21.2–22.2 | 4.19–4.501 | vw–m |
| 22.5–23.45 | 3.95–3.793 | vw–m |
| 26.5–27.9 | 3.351–3.198 | vw–m |

TABLE W

| | (BAPSO-47) | |
|---|---|---|
| 2θ | d (Å) | Relative Intensity |
| 9.4–9.6 | 9.41–9.21 | vs |
| 12.8–13.1 | 6.92–6.76 | vw–m |
| 16.0–16.3 | 5.54–5.44 | vw–m |
| 20.5–21.0 | 4.31–4.23 | m–vs |
| 24.6–25.3 | 3.613–3.526 | vw–m |
| 30.6–31.1 | 2.921–2.876 | vw–m |

TABLE X

| | (BAPSO-51) | |
|---|---|---|
| 2θ | d (Å) | Relative Intensity |
| 7.9–8.1 | 11.91–10.91 | w–s |
| 11.8–12.0 | 7.50–7.38 | m–vs |
| 13.7–13.9 | 6.46–6.37 | m–vs |
| 18.1–18.4 | 4.90–4.82 | w–s |
| 22.8–23.1 | 3.900–3.850 | v–vs | which process comprises providing a reaction mixture composition at an effective temperature and for an effective time sufficient to produce said molecular sieves, said reaction mixture composition being expressed in terms of molar oxide ratios as follows:

$$mR : (B_sAl_tP_uSi_v)O_2 : bH_2O$$

wherein "R" is an organic templating agent; "a" is the amount of "R" and is an effective amount greater than zero to about 6; "b" has a value of from zero to about 500; and "s", "t", "u" and "v" represent the mole fractions, respectively, of boron, aluminum, phosphorus and silicon in the $(B_sAl_tP_uSi_v)O_2$ constituent, and each has a value of at least 0.01.

15. Process according to claim 14 wherein "s", "t", "u" and "v" are within the area defined by points F, G, H, I and J of FIG. 3.

16. Process according to claim 14 wherein "a" is not greater than about 0.5.

17. Process according to claim 14 wherein "b" is not greater than about 20.

18. Process according to claim 14 wherein the source of phosphorus in the reaction mixture is orthophosphoric acid.

19. Process according to claim 18 wherein the source of phosphorus in the reaction mixture is orthophosphoric acid and the source of aluminum is at least one compound selected from the group consisting of pseudo-boehmite and aluminum alkoxides.

20. Process according to claim 19 wherein the aluminum alkoxide is selected from the group consisting of aluminum isopropoxide, tri-sec-butoxide and hexadecoxide.

21. Process according to claim 14 wherein the silicon source is silica or a tetraalkyl orthosilicate.

22. Process according to claim 14 wherein the source of boron is selected from the group consisting of oxides, hydroxides, alkoxides, chlorides, bromides, iodides, sulfates, nitrates, carboxylates and mixtures thereof.

23. Process according to claim 14 wherein the source of boron is selected from the group consisting of boric acid and trialkyl borates.

24. Process according to claim 14 wherein the reaction mixture composition contains from about 1.0 to about 1.5 total moles of boron and silicon per mole of phosphorus.

25. Process according to claim 14 wherein the reaction mixture composition contains from about 0.75 to about 1.25 moles of aluminum per mole of phosphorus.

26. Process according to claim 14 wherein the organic templating agent is a quaternary ammonium or quaternary phosphonium compound having the formula:

$R_4X^+$ wherein X is nitrogen or phosphorus and each R is an alkyl or aryl group containing from 1 to 8 carbon atoms.

27. Process according to claim 14 wherein the organic templating agent is an amine.

28. Process according to claim 14 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethylpiperazine; 1,4-diaziabicyclo-(2,2,2)octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrrolidine; 2-imidazolidone; di-n-propylamine; and a polymeric quaternary ammonium salt $_x$ wherein x is a value of at least 2.

29. Molecular sieve prepared by calcining, at a temperature sufficiently high to remove at least some of any organic templating agent present in the intracrystalline pore system, a crystalline molecular sieve having three-dimensional microporous framework structures of $BO_2$, $AlO_2$, $PO_2$ and $SiO_2$ tetrahedral units having an empirical chemical composition on an anhydrous basis expressed by the formula:

$mR : (B_wAl_xP_ySi_z)O_2$ wherein "R" represents at least one organic templating agent present in the intracrystalline pore system; "m" represents the molar amount of "R" present per mole of $(B_wAl_xP_ySi_z)O_2$ and has a value of zero to about 0.3; and "w", "x", "y" and "z" represent the mole fractions of boron, aluminum, phosphorus and silicon, respectively, present as tetrahedral oxides, said mole fractions being such that they are within the pentagonal compositional area defined by points A, B, C, D, and E of FIG. 1, said crystalline molecular sieves having a characteristic X-ray powder diffraction pattern which contains at least the d-spacings set forth in one of the following Tables C, F, J, N, P, T, V, W and X

TABLE C

| | (BAPSO-14) | |
|---|---|---|
| 2θ | d (Å) | Relative Intensity |
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE F

| | (BAPSO-18) | |
|---|---|---|
| 2θ | d (Å) | Relative Intensity |
| 9.6–9.65 | 9.21–9.16 | vs |
| 15.5–15.55 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE H

| | (BAPSO-31) | |
|---|---|---|
| 2θ | d(Å) | Relative Intensity |
| 8.4–9.5 | 10.53–9.31 | w–s |
| 20.2–20.4 | 4.40–4.35 | m |
| 22.0–22.1 | 4.040–4.022 | m |
| 22.5–22.7 | 3.952–3.92 | vs |
| 31.6–31.8 | 2.831–2.814 | w–m |

TABLE N

| | (BAPSO-36) | |
|---|---|---|
| 2θ | d (Å) | Relative Intensity |
| 7.45–8.0 | 11.14–11.05 | vs |
| 8.1–8.3 | 10.91–10.65 | w–m |
| 16.3–16.6 | 5.44–5.34 | w–m |
| 18.9–19.4 | 4.70–4.57 | w–m |
| 20.7–21.0 | 4.29–4.23 | w–m |

TABLE P

| | (BAPSO-39) | |
|---|---|---|
| 2θ | d (Å) | Relative Intensity |
| 9.2–9.6 | 9.61–9.21 | m |
| 13.1–13.5 | 6.76–6.56 | m |
| 17.8–18.4 | 4.98–4.82 | w–m |
| 20.8–21.3 | 4.27–4.17 | m–vs |
| 22.2–22.85 | 4.00–3.892 | m–vs |
| 26.4–27.05 | 3.376–3.296 | w–m |

TABLE T

| | (BAPSO-43) | |
|---|---|---|
| 2θ | d (Å) | Relative Intensity |
| 12.3–12.95 | 7.20–6.83 | m–vs |
| 16.8–17.45 | 5.28–5.09 | vw–w |
| 21.45–21.85 | 4.145–4.071 | m–vs |
| 27.1–27.85 | 3.291–3.232 | w–vs |
| 32.4–33.2 | 2.763–2.699 | vw–m |

TABLE V

| | (BAPSO-46) | |
|---|---|---|
| 2θ | d (Å) | Relative Intensity |
| 7.2–8.1 | 12.28–10.92 | vs |
| 12.9–13.6 | 6.86–6.51 | vw |
| 21.2–22.2 | 4.19–4.501 | vw–m |
| 22.5–23.45 | 3.95–3.793 | vw–m |
| 26.5–27.9 | 3.351–3.198 | vw–m |

TABLE W

| | (BAPSO-47) | |
|---|---|---|
| 2θ | d (Å) | Relative Intensity |
| 9.4–9.6 | 9.41–9.21 | vs |
| 12.8–13.1 | 6.92–6.76 | vw–m |
| 16.0–16.3 | 5.54–5.44 | vw–m |
| 20.5–21.0 | 4.31–4.23 | m–vs |
| 24.6–25.3 | 3.613–3.526 | vw–m |

TABLE W-continued (BAPSO-47)

| 2θ | d (Å) | Relative Intensity |
|---|---|---|
| 30.6–31.1 | 2.921–2.876 | vw–m |

TABLE X (BAPSO-51)

| 2θ | d (Å) | Relative Intensity |
|---|---|---|
| 7.9–8.1 | 11.91–10.91 | w–s |
| 11.8–12.0 | 7.50–7.38 | m–vs |
| 13.7–13.9 | 6.46–6.37 | m–vs |
| 18.1–18.4 | 4.90–4.82 | w–s |
| 22.8–23.1 | 3.900–3.850 | v–vs. |

\* \* \* \* \*

UNITED STATES PATENT AND TRADEMARK OFFICE
CERTIFICATE OF CORRECTION

PATENT NO. : 5,057,295
DATED : October 15, 1991
INVENTOR(S) : Flanigen et al.

It is certified that error appears in the above-identified patent and that said Letters Patent is hereby corrected as shown below:

In Column 28, Table V, last line, left column:
        Change "26.5-27.9" to --26.6-27.9

Signed and Sealed this

Twenty-sixth Day of January, 1993

Attest:

STEPHEN G. KUNIN

*Attesting Officer*      *Acting Commissioner of Patents and Trademarks*

UNITED STATES PATENT AND TRADEMARK OFFICE
CERTIFICATE OF CORRECTION

PATENT NO. : 5,057,295
DATED : October 15, 1991
INVENTOR(S) : Flanigen et al.

It is certified that error appears in the above-identified patent and that said Letters Patent is hereby corrected as shown below:

In Column 28, Table V, last line, left column:
　　　　　　Change "26.5-27.9" to --26.6-27.9

Signed and Sealed this

Second Day of February, 1993

Attest:

STEPHEN G. KUNIN

*Attesting Officer*　　　*Acting Commissioner of Patents and Trademarks*